(12) United States Patent
Hamachi et al.

(10) Patent No.: US 12,049,610 B2
(45) Date of Patent: Jul. 30, 2024

(54) APPARATUS FOR PRODUCING AN ORGANIC SUBSTANCE

(71) Applicant: SEKISUI CHEMICAL CO., LTD., Osaka (JP)

(72) Inventors: Kokoro Hamachi, Ibaraki (JP); Kanetomo Sato, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 815 days.

(21) Appl. No.: 17/040,134

(22) PCT Filed: Mar. 20, 2019

(86) PCT No.: PCT/JP2019/011909
§ 371 (c)(1),
(2) Date: Sep. 22, 2020

(87) PCT Pub. No.: WO2019/188727
PCT Pub. Date: Oct. 3, 2019

(65) Prior Publication Data
US 2021/0079327 A1 Mar. 18, 2021

(30) Foreign Application Priority Data
Mar. 26, 2018 (JP) ................. 2018-058246

(51) Int. Cl.
*C12M 1/107* (2006.01)
*C12N 1/20* (2006.01)
*C12P 7/06* (2006.01)
*C12R 1/145* (2006.01)

(52) U.S. Cl.
CPC ............. *C12M 21/04* (2013.01); *C12P 7/065* (2013.01); *C12N 1/205* (2021.05); *C12R 2001/145* (2021.05)

(58) Field of Classification Search
CPC ...... C12M 21/04; C12M 21/12; C12M 29/26; C12N 1/205; C12P 7/065; C12P 7/06; C12R 2001/145; Y02E 50/10
See application file for complete search history.

(56) References Cited

U.S. PATENT DOCUMENTS

| 2002/0079266 A1* | 6/2002 | Ainsworth | ............... C02F 3/28 210/603 |
| 2009/0035832 A1* | 2/2009 | Koshland, Jr. | ............ C12P 1/04 435/292.1 |

(Continued)

FOREIGN PATENT DOCUMENTS

| CN | 1238712 A | 12/1999 |
| CN | 105112286 A | 12/2015 |

(Continued)

OTHER PUBLICATIONS

International Search Report for Application No. PCT/JP2019/011909, mailed on Jun. 18, 2019.
(Continued)

*Primary Examiner* — Michael L Hobbs (57) ABSTRACT

Provided is a device for continuously manufacturing an organic substance with high productivity, in which a means is installed whereby a synthesis gas having a specific nutrient source concentration for microbes in a continuous fermenter is stored with good efficiency and the gas composition thereof is made uniform in a stage prior to supplying the synthesis gas to the fermenter including microbes, so that uniformity of the synthesis gas composition is ensured. A device for manufacturing an organic substance, provided with a gas generating unit for gasifying a carbon source and generating a starting material gas, a gas supply unit for supplying a synthesis gas including the starting material gas to a fermenter, and a fermenter for microbial fermentation of the synthesis gas in the fermenter, a gas circulation unit for (Continued)

making the gas composition uniform being further provided between the gas generating unit and the gas supply unit or to the gas supply unit.

16 Claims, 5 Drawing Sheets

(56) References Cited

U.S. PATENT DOCUMENTS

| | | | |
|---|---|---|---|
| 2013/0078689 A1 | 3/2013 | Hickey | |
| 2013/0316411 A1* | 11/2013 | Schultz | C12M 43/00 435/163 |
| 2016/0222340 A1 | 8/2016 | Satou et al. | |
| 2017/0183618 A1 | 6/2017 | Satou et al. | |

FOREIGN PATENT DOCUMENTS

| | | |
|---|---|---|
| JP | 3-127983 A | 5/1991 |
| JP | 2002-533202 A | 10/2002 |
| JP | 2016-029921 A | 3/2016 |
| WO | 00/38497 A | 7/2000 |
| WO | 03/051803 A1 | 6/2003 |
| WO | 2015/037710 A1 | 3/2015 |
| WO | 2016/017573 A1 | 2/2016 |

OTHER PUBLICATIONS

Supplementary European Search Report for Application No. 19776215.6 mailed on Nov. 24, 2021, 8 pages.

\* cited by examiner

FIG.7

APPARATUS FOR PRODUCING AN ORGANIC SUBSTANCE

This application is a national phase entry of International Application No. PCT/JP2019/011909 filed on Mar. 20, 2019, which claims the benefit of Japanese Application No. 2018-058246 filed on Mar. 26, 2018, each of which is incorporated by reference in its entirety.

TECHNICAL FIELD

The present invention relates to an apparatus for producing an organic substance, and in particular relates to an apparatus for producing an organic substance using a fermented liquid obtained by microbial transformation of a specific synthesis gas.

BACKGROUND ART

In recent years, methods for producing various organic substances with a raw material other than petroleum, for example, a method for producing bioethanol from an edible material such as corn by a sugar fermentation process, have been attracting attention, with the concern about depletion of fossil fuel resources and in consideration of global environmental problems such as increase of carbon dioxide in the air.

However, the problem with such a sugar fermentation process using an edible material is that they cause a rise in food prices because the limited farmland area is used for producing materials other than food. To solve this problem, various methods and apparatuses have been studied to produce organic substances using substances as raw materials which have been discarded.

For example, Patent Document 1 discloses an apparatus for manufacturing an organic substance, comprising a syngas producing furnace for producing syngas containing carbon monoxide by partially oxidizing a carbon source, an organic substance synthesis unit for producing an organic substance from the syngas, a moisture content raising unit for raising the moisture content of the syngas, which is disposed between the syngas producing furnace and the organic substance synthesis unit, and a moisture content lowering unit for lowering the moisture content of the syngas, which is disposed between the moisture content raising unit and the organic substance synthesis unit.

Furthermore, Patent Document 2 discloses an apparatus for producing an organic substance from waste, comprising a synthesis gas generation furnace for generating a synthesis gas by partial oxidization of waste, a fermenter containing a microorganism which produces an organic substance from the synthesis gas, and a nutrient feeder for feeding a solid or liquid nutrient to the fermenter when the amount of the synthesis gas fed to the fermenter is insufficient.

Patent Document 3 also discloses an apparatus for producing an organic substance, comprising an organic substance synthesis unit for producing an organic substance by microbial fermentation, a heating unit for heating a solution from the organic substance synthesis unit, a separation unit for separating solid components in the solution heated, and an extraction unit for extracting the organic substance from the solution from which the solid components have been separated.

PRIOR ART DOCUMENTS

Patent Document

Patent Document 1: International Publication No. 2015/037710
Patent Document 2: International Publication No. 2016/017573
Patent Document 3: JP 2016-29921 A

SUMMARY OF INVENTION

Technical Problem

Studies by the present inventors have shown that when the apparatuses for production as disclosed in Patent Documents 1 to 3 are employed using industrial gas or exhaust gas from steel mills as a raw material gas, the composition of gas to be introduced into the fermenter (organic substance synthesis unit) containing microorganisms is relatively uniform over time, and thus problems are less likely to occur.

However, when the apparatuses for production as disclosed in Patent Documents 1 to 3 are used to produce a raw material gas by using, for example, an inexpensive waste as a carbon source, the presence of impurities and non-uniform components, which are peculiar to wastes, cause a very sharp change with time in the amount of various impurities and the uniformity of the components in the gas to be introduced into the fermenter (organic substance synthesis unit) containing microorganisms, causing the problem with production of the target organic substance. It has also been found that introducing synthesis gas from a gas producing furnace into the fermenter (organic substance synthesis unit) through a conventional gas storage unit equipped with a partition plate or a stirring blade is not effective for the above problem because the gas composition is not always sufficiently uniform.

The present inventors have conducted further studies and have found that upon the feeding of synthesis gas, high stress unfavorable for microorganisms in the fermenter is produced when a large amount of impurities are instantaneously fed, rather than when a constant amount of impurities are continuously fed, inhibiting the desired microbial fermentation to cause problems. The present inventors have found that particularly when gasification is performed using inexpensive wastes as a carbon source, the amount of impurities in the synthesis gas continuously fed to the fermenter frequently fluctuates to as high as 1,000 times, for example, in a few minutes, and when such a synthesis gas is fed, a conventional apparatus for producing an organic substance is incapable of dealing with these situations.

The present invention has been made in order to solve the above problems, and an object thereof is to provide an apparatus for producing an organic substance continuously at high productivity, by providing a means which can store synthesis gas efficiently and make the gas composition uniform before feeding the gas to a continuous fermenter containing microorganisms, so as to ensure the uniformity of the synthesis gas composition having a concentration of a specific nutritional source for microorganisms in the fermenter.

Another object of the present invention is to provide a method for producing an organic substance continuously at high productivity, the method comprising feeding a synthesis gas having a specific nutritional source to a continuous fermenter so as to ensure the uniformity of a concentration of a specific nutritional source for microorganisms in the fermenter.

Solution to Problem

The present inventors have conducted intensive studies on the method for solving the above problem, and have found that by providing a means which can store synthesis gas efficiently and make the gas composition uniform between a gas generating unit for generating a raw material gas by gasification of a carbon source and a fermenter containing microorganisms, the synthesis gas continuously fed to the fermenter is made more uniform, and thus an organic substance can be produced continuously at high productivity.

The present inventors have conducted intensive studies on the method for solving the above problem, and have also found that by feeding a synthesis gas containing a specific amount of nutritional sources (an N source, a P source and an S source) for microorganisms to a fermenter, the concentration of the nutritional sources in the continuous fermenter can be prevented from being non-uniform, and thus an organic substance can be produced continuously at high productivity.

Accordingly, the gist of the present invention is as follows:

[1] An apparatus for producing an organic substance by microbial fermentation of a gas containing at least carbon monoxide and hydrogen, the apparatus comprising a gas generating unit for generating a raw material gas by gasification of a carbon source, a gas feeding unit for feeding a synthesis gas comprising the raw material gas to a fermenter containing a microorganism, a fermenter for microbial fermentation of the synthesis gas, and further a gas circulating unit for making the gas composition uniform, which is disposed between the gas generating unit and the gas feeding unit, or in the gas feeding unit.

[2] The apparatus for producing an organic substance according to [1], wherein the gas circulating unit comprises a plurality of gas storage units and a plurality of gas pipes connecting the gas storage units.

[3] The apparatus for producing an organic substance according to [1] or [2], wherein a pressurizer is connected to at least one of the gas pipes to pressurize and thus circulate gas in the pipes.

[4] The apparatus for producing an organic substance according to any one of [1] to [3], wherein the capacity of at least one upstream gas storage unit out of the plurality of gas storage units is smaller than the capacity of at least one downstream gas storage unit.

[5] The apparatus for producing an organic substance according to any one of [1] to [4], wherein the capacity of the most upstream gas storage unit out of the plurality of gas storage units is half or less of the capacity of the most downstream storage unit.

[6] The apparatus for producing an organic substance according to any one of [1] to [5], wherein gas is retained in the gas circulating unit for at least a minute and then fed to the fermenter.

[7] The apparatus for producing an organic substance according to any one of [1] to [6], wherein the carbon source comprises waste.

[8] The apparatus for producing an organic substance according to any one of [1] to [7], further comprising a means for reducing the concentration of sulfur in the raw material gas to obtain the synthesis gas.

[9] The apparatus for producing an organic substance according to any one of [1] to [8], wherein the fermenter comprises a *Clostridium* species as the microorganism.

[10] The apparatus for producing an organic substance according to any one of [1] to [9], wherein the organic substance is ethanol.

The gist of the present invention is also as follows:

[1] A method for producing an organic substance by microbial fermentation of a synthesis gas containing at least carbon monoxide and hydrogen, the method comprising a synthesis gas feeding step of feeding a synthesis gas to a fermenter containing a microorganism and a fermentation step of carrying out microbial fermentation of the synthesis gas in the fermenter, wherein the synthesis gas comprises 0.01 ppm or more and 90 ppm or less of at least one compound selected from the group consisting of a sulfur compound, a phosphorus compound and a nitrogen compound.

[2] The method for producing an organic substance according to [1], wherein the synthesis gas further comprises 0.01 ppm or more and 90 ppm or less of an aromatic compound.

[3] The method for producing an organic substance according to [1] or [2], further comprising a raw material gas production step of producing a raw material gas by gasification of a carbon source and a pretreatment step of reducing the concentration of sulfur in the raw material gas to obtain the synthesis gas.

[4] The method for producing an organic substance according to [3], wherein the pretreatment step comprises a step of passing the raw material gas through a desulfurizer.

[5] The method for producing an organic substance according to any one of [1] to [4], wherein the fermenter comprises a microorganism of the genus *Clostridium*.

[6] The method for producing an organic substance according to any one of [1] to [5], wherein the organic substance is ethanol.

[7] The method for producing an organic substance according to any one of [1] to [6], wherein the sulfur compound in the synthesis gas is sulfur dioxide.

Advantageous Effects of Invention

According to the present invention, an organic substance can be produced in a stable manner for a long time by reducing stress on microorganisms caused by a sharp change in synthesis gas composition even when a synthesis gas, for example, containing impurities and having a non-uniform gas composition is continuously fed to a fermenter containing microorganisms.

In particular, the sharp change in synthesis gas composition is especially significant, for example, when an inexpensive waste containing a lot of impurities is gasified as a carbon source and a synthesis gas containing the same is continuously introduced into a fermenter containing microorganisms, and thus using the present invention is particularly effective in such cases.

Furthermore, according to the present invention, an organic substance can be produced at high productivity because uneven concentration of nutritional sources in the fermenter can be suppressed. In addition, when a synthesis gas derived from waste is used, the raw material gas contains a large amount of nutritional sources, and thus productivity can be easily improved by controlling the content of the nutritional sources in the gas in each unit and then feeding the gas to the fermenter. Furthermore, the present invention has a secondary advantage of being able to reduce the cost for purchasing various nutritional sources for medium.

DESCRIPTION OF EMBODIMENTS

Hereinafter, an example of preferred embodiments of the present invention will be described. The following embodiments are examples for describing the present invention, and the present invention is not at all limited to the following embodiments.

In the present description, the proportion of gas components is based on the volume, not weight, unless otherwise specified. Thus, percentage % represents % by volume and ppm represents ppm by volume unless otherwise specified.

First Embodiment

Figure 1:
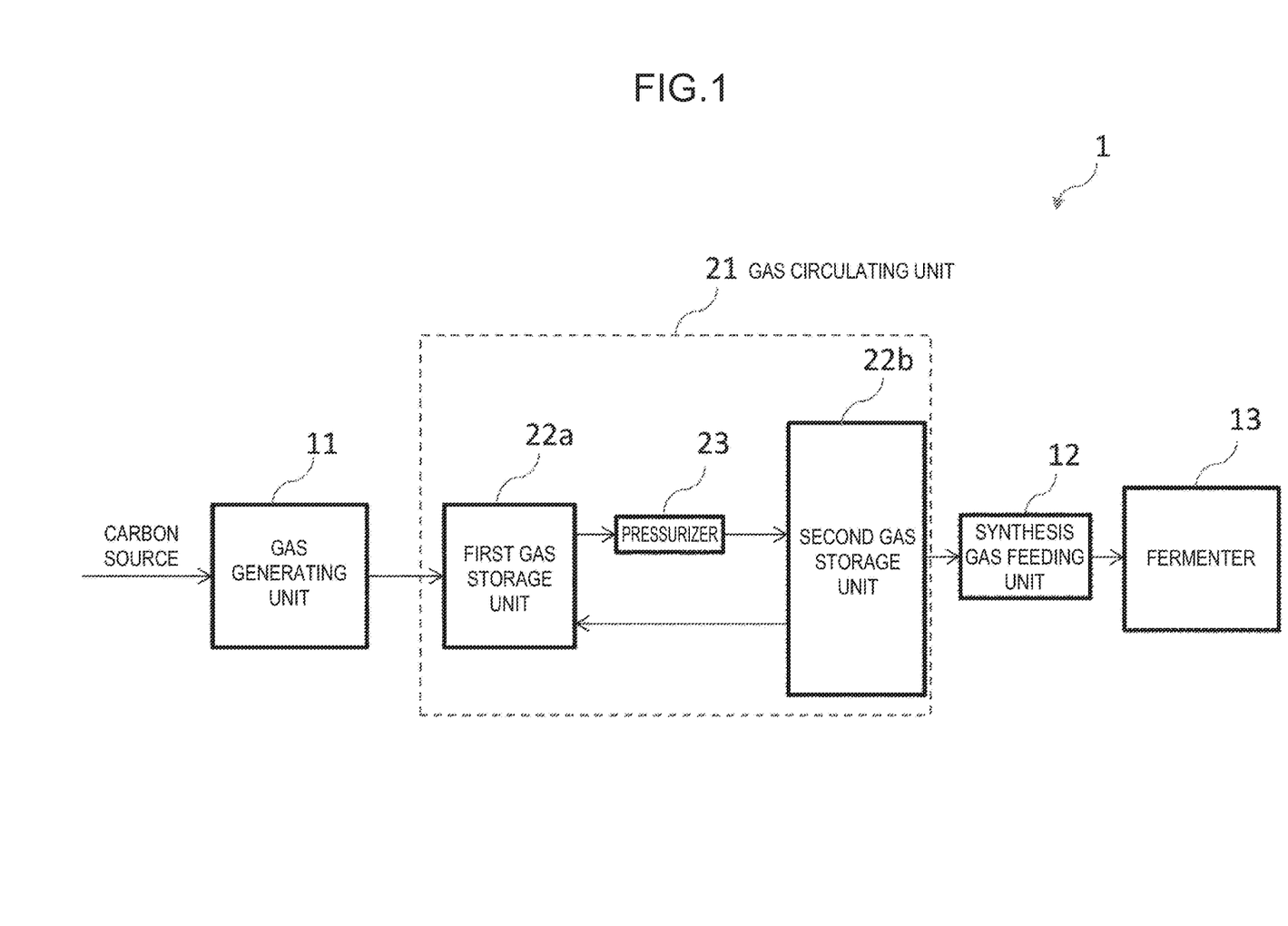
FIG. 1 is a schematic view of an apparatus for producing an organic substance according to a first embodiment.

FIG. 1 is a schematic view of an apparatus for producing an organic substance from a carbon source such as waste according to a first embodiment of the present invention. A production apparatus 1 is an apparatus for producing an organic substance by microbial fermentation of gas containing at least carbon monoxide and hydrogen, and has a gas generating unit 11 for generating a raw material gas by gasification of the carbon source, a synthesis gas feeding unit 12 for feeding a synthesis gas containing a raw material gas to a fermenter 13 containing microorganisms, and a fermenter 13 for microbial fermentation of the synthesis gas in the fermenter 13. The production apparatus 1 also has a gas circulating unit 21 for making the gas composition uniform, which is disposed between the gas generating unit 11 and the synthesis gas feeding unit 12.

The gas circulating unit 21 has two gas storage units, a first gas storage unit 22a and a second gas storage unit 22b, and has a plurality of gas pipes connecting them. A pressurizer 23 is connected to the gas pipe between the first gas storage unit 22a and the second gas storage unit 22b. The pressurizer 23 presses the gas in the pipe and the gas circulates in the gas circulating unit 21.

It is preferable that the capacity of the upstream first gas storage unit 22a of the two gas storage units is smaller than the capacity of the downstream second gas storage unit 22b.

The capacity of the upstream first gas storage unit 22a is preferably half or less, more preferably ⅕ or less, and most preferably ¹⁄₁₅ or less of the capacity of the downstream second gas storage unit 22b.

Furthermore, gas is retained in the gas circulating unit for at least a minute, preferably 3 minutes, and more preferably 5 minutes, and then fed to the fermenter.

The gas circulating unit 21 with the above configuration makes the synthesis gas continuously fed to the fermenter 13 more uniform and enables continuous production of an organic substance at high productivity. In particular, an organic substance can be produced in a stable manner for a long time by reducing stress on microorganisms caused by a sharp change in synthesis gas composition even when an inexpensive waste containing a lot of impurities is used as a carbon source and a synthesis gas is continuously fed to the fermenter 13.

In FIG. 1, although the synthesis gas feeding unit 12 is on the downstream of the gas circulating unit 21, a mode in which the gas feeding unit 12 is on the upstream of the gas circulating unit 21 may also be employed.

Second Embodiment

Figure 2:
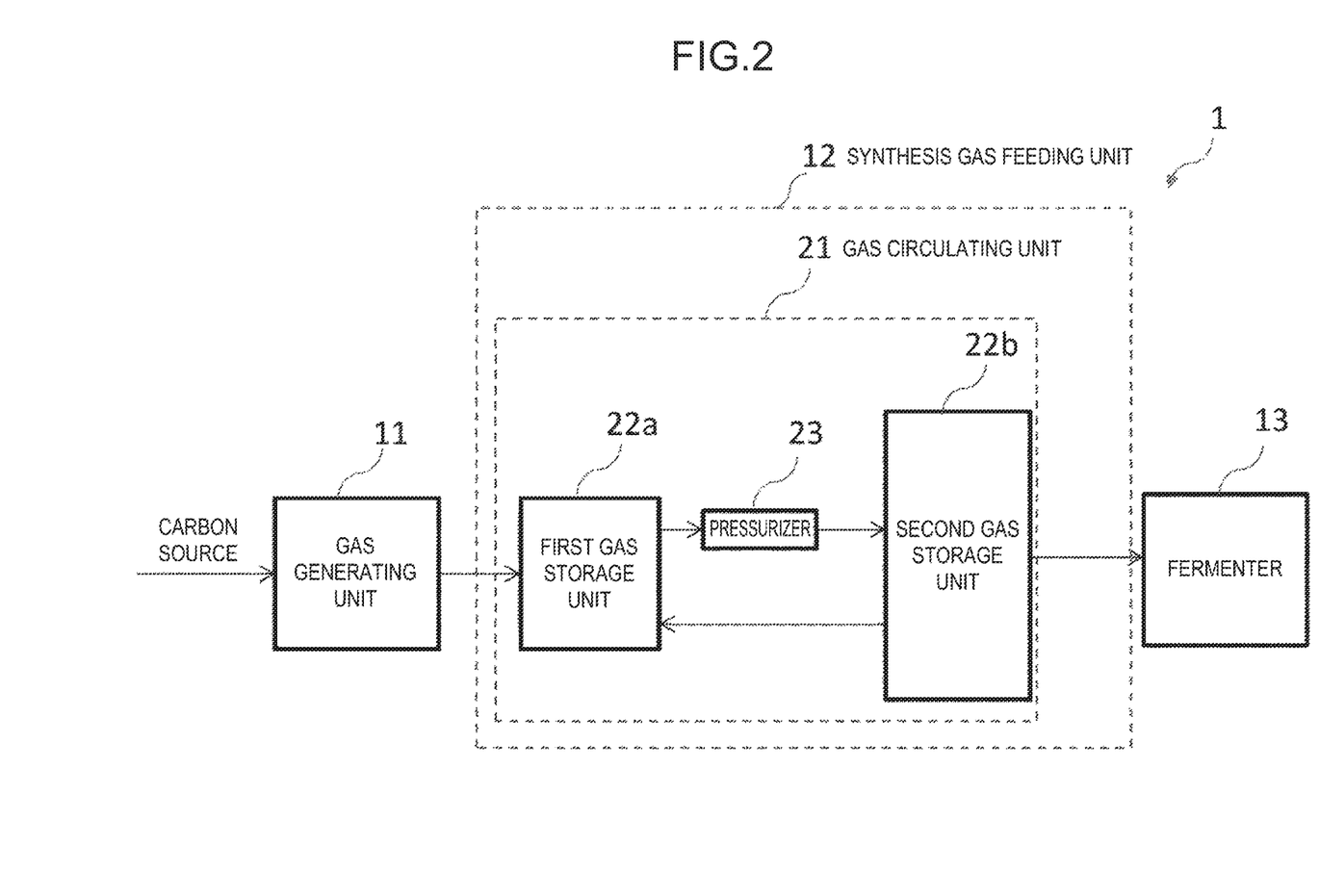
FIG. 2 is a schematic view of an apparatus for producing an organic substance according to a second embodiment.

FIG. 2 is a schematic view of an apparatus for producing an organic substance from a carbon source such as waste according to a second embodiment of the present invention. FIG. 2 is different from FIG. 1 in that the production apparatus 1 further has a gas circulating unit 21 in the synthesis gas feeding unit, not between the gas generating unit 11 and the synthesis gas feeding unit 12. Using such a configuration can simplify the structure compared to the production apparatus of the first embodiment.

The second embodiment of the present invention has the same excellent properties as the first embodiment. More specifically, the gas circulating unit 21 with the above configuration makes the synthesis gas continuously fed to the fermenter 13 more uniform and enables continuous production of an organic substance at high productivity. In particular, an organic substance can be produced in a stable manner for a long time by reducing stress on microorganisms caused by a sharp change in synthesis gas composition even when an inexpensive waste containing a lot of impurities is used as a carbon source and a synthesis gas is continuously fed to the fermenter 13.

Third Embodiment

Figure 3:
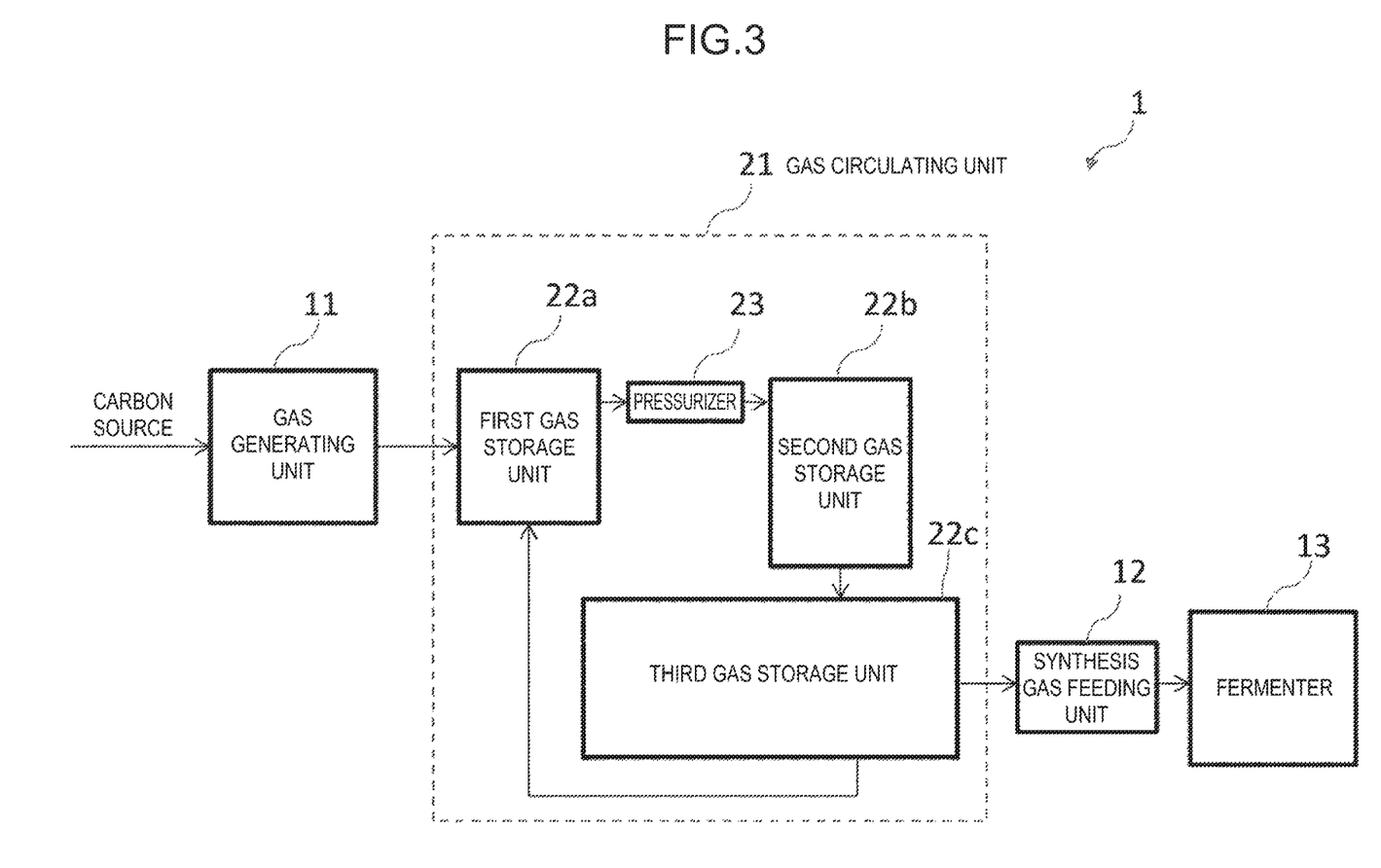
FIG. 3 is a schematic view of an apparatus for producing an organic substance according to a third embodiment.

FIG. 3 is a schematic view of an apparatus for producing an organic substance from a carbon source such as waste according to a third embodiment of the present invention. FIG. 3 is different from FIG. 1 in that the gas circulating unit 21 has not two but three gas storage units, i.e., the first gas storage unit 22a, the second gas storage unit 22b and the third gas storage unit 22c, and has a plurality of gas pipes connecting them.

It is preferable that the capacity of the first gas storage unit 22a out of the three gas storage units is smaller than the capacity of the second gas storage unit 22b and/or the third gas storage unit 22c, and the capacity of the second gas storage unit 22b is smaller than the capacity of the third gas storage unit 22c.

The capacity of the most upstream first gas storage unit 22a is preferably half or less, more preferably ⅕ or less, and most preferably ¹⁄₁₅ or less of the capacity of the most downstream third gas storage unit 22c.

Furthermore, gas is retained in the gas circulating unit for at least a minute, preferably 3 minutes, and more preferably 5 minutes, and then fed to the fermenter.

The gas circulating unit 21 with the above configuration makes the synthesis gas continuously fed to the fermenter 13 more uniform and enables continuous production of an organic substance at high productivity. In particular, an organic substance can be produced in a stable manner for a long time by reducing stress on microorganisms caused by a sharp change in synthesis gas composition even when an inexpensive waste containing a lot of impurities is used as a carbon source and a synthesis gas is continuously fed to the fermenter 13.

Hereinafter, the substance used in the production apparatus of the present invention will be described in detail.

I. Substances

<Synthesis Gas>

The synthesis gas in the present invention contains at least carbon monoxide and hydrogen, and 0.01 ppm or more and 90 ppm or less of at least one compound selected from the group consisting of a sulfur compound, a phosphorus compound and a nitrogen compound. Each content of the above compounds is preferably 0.05 ppm or more, more preferably 0.1 ppm or more, further preferably 0.5 ppm or more, and preferably less than 80 ppm, more preferably 70 ppm or less, further preferably 60 ppm or less, and still more preferably 40 ppm or less. When the content ratio is the lower limit or more, microorganisms are likely to be cultured well. When the content ratio is the upper limit or less, the medium is less likely to be contaminated by various nutrient sources which microorganisms have not consumed.

Examples of sulfur compounds include sulfur dioxide, $CS_2$, COS, $H_2S$, and in particular $H_2S$ and sulfur dioxide are preferred because they are an easy-to-consume nutrient source for microorganisms. Thus, it is more preferable that the total amount of $H_2S$ and sulfur dioxide in synthesis gas be in the above range, and it is particularly preferable that the amount of sulfur dioxide alone be in the above range.

Phosphoric acid is preferred as the phosphorus compound because it is an easy-to-consume nutrient source for microorganisms. Thus, it is more preferable that the synthesis gas contains phosphoric acid in the above range.

Examples of nitrogen compounds include nitrogen monoxide, nitrogen dioxide, acrylonitrile, acetonitrile and HCN. HCN is preferred because it is an easy-to-consume nutrient source for microorganisms. Thus, it is more preferable that the synthesis gas contains HCN in the above range.

The synthesis gas in the present invention may further contain 0.01 ppm or more and 90 ppm or less of an aromatic compound. The content ratio of the above aromatic compound is preferably 0.03 ppm or more, more preferably 0.05 ppm or more, and further preferably 0.1 ppm or more, and preferably 70 ppm or less, more preferably 50 ppm or less, and further preferably 30 ppm or less. When the content ratio is the lower limit or more, microorganisms are likely to be cultured well. When the content ratio is the upper limit or less, medium is less likely to be contaminated by various nutrient sources which microorganisms have not consumed. Examples of aromatic compounds include benzene, toluene, ethylbenzene, xylene and styrene. A particularly preferred aromatic compound is xylene.

As described later, for the synthesis gas in the present invention, first a raw material gas is produced by gasification of a carbon source (raw material gas production step), and then the gas is subjected to a step of reducing sulfur concentration in the raw material gas (pretreatment step), and the resulting gas may be used as the synthesis gas. The raw material gas may be prepared in the form of a gas containing carbon monoxide as the main component, by a heat treatment of burning carbon source (incomplete combustion), in other words, by partly oxidizing carbon source. The resulting gas may contain gas components such as hydrogen, water vapor, carbon dioxide, nitrogen and oxygen in addition to carbon monoxide, and may also contain other components such as soot, tar, a nitrogen compound, a sulfur compound and an aromatic compound.

In this regard, the carbon source to be subjected to the above heat treatment, i.e., gasification, is not particularly limited. For example, various carbon-containing materials such as waste and exhaust gas from steel mills, general waste, and combustion gas from waste incinerators may also be suitably used for the purpose of recycling. For example, as the carbon source, by-products obtained in an industrial process such as manufacture of ferrous products, manufacture of non-ferrous products, a petroleum refining process and electric power generation, and modified gas such as biomass gas, natural gas, shale gas and associated petroleum gas may also be used. Utilizing wastes to be discarded as a carbon source is important not only economically but also in the consideration of the ecological system. Examples of such waste also include plastic waste, garbage, municipal solid waste (MSW), waste tires, biomass waste, household waste such as Japanese futon and paper and construction members. One of them may be subjected to the gasification treatment singly or two or more of them may be subjected thereto in combination. When the raw material gas is derived from waste, the raw material gas usually contains 1 ppm or more of a nitrogen compound, 100 ppm or more of a sulfur compound, 0.1 ppm or more of a phosphorus compound, and 100 ppm or more of an aromatic compound. Since such waste contains a large amount of, particularly a sulfur compound and an aromatic compound, it is preferable that their content be adjusted to a suitable content in the pretreatment equipment described later before being fed to the continuous fermenter.

<Microorganism>

The microorganism (species) in the present invention is not particularly limited as long as a desired organic substance can be produced by microbial fermentation of the synthesis gas according to the present invention, which contains carbon monoxide as the main raw material. For example, a microorganism (species) that produces an organic substance from the synthesis gas according to the present invention by the fermentation action of gas utilizing bacteria may be preferably used. In particular, *Clostridium autoethanogenum* is preferred, but the microorganism is not limited thereto. In the following, those microorganisms will be described in more detail.

The above gas utilizing bacteria include both eubacteria and archaea.

Examples of eubacteria include bacteria of the genus *Clostridium*, bacteria of the genus *Moorella*, bacteria of the genus *Acetobacterium*, bacteria of the genus *Carboxydocella*, bacteria of the genus *Rhodopseudomonas*, bacteria of the genus *Eubacterium*, bacteria of the genus *Butyribacterium*, bacteria of the genus *Oligotropha*, bacteria of the genus *Bradyrhizobium*, and bacteria of the genus *Ralsotonia*, which are aerobic hydrogen oxidizing bacteria.

Meanwhile, examples of archaea include bacteria of the genus *Methanobacterium*, bacteria of the genus *Methanobrevibacter*, bacteria of the genus *Methanocalculus*, bacteria of the genus *Methanococcus*, bacteria of the genus *Methanosarcina*, bacteria of the genus *Methanosphaera*, bacteria of the genus *Methanothermobacter*, bacteria of the genus *Methanothrix*, bacteria of the genus *Methanoculleus*, bacteria of the genus *Methanofollis*, bacteria of the genus *Methanogenium*, bacteria of the genus *Methanospirillium*, bacteria of the genus Methanosaeta, bacteria of the genus *Thermococcus*, bacteria of the genus *Thermofilum*, and bacteria of the genus *Arcaheoglobus*. Of them, bacteria of the genus *Methanosarcina*, bacteria of the genus *Methanococcus*, bacteria of the genus *Methanothermobacter*, bacteria of the genus *Methanothrix*, bacteria of the genus *Thermococcus*, bacteria of the genus *Thermofilum*, and bacteria of the genus *Archaeoglobus* are preferred as an archaeon.

Furthermore, bacteria of the genus *Methanosarcina*, bacteria of the genus *Methanothermobactor*, or bacteria of the genus *Methanococcus* are preferred, and bacteria of the genus *Methanosarcina* or bacteria of the genus *Methanococcus* are particularly preferred as archaea because they have excellent properties of utilizing carbon monoxide and carbon dioxide. Specific examples of bacteria of the genus *Methanosarcina* include *Methanosarcina barkeri*, *Methanosarcina mazei* and *Methanosarcina acetivorans*.

Of such gas utilizing bacteria, a bacterium which is highly capable of producing the target organic substance is selected and used. Examples of gas utilizing bacteria highly capable of producing ethanol include *Clostridium autoethanogenum*, *Clostridium ljungdahlii*, *Clostridium aceticum*, *Clostridium carboxidivorans*, *Moorella thermoacetica* and *Acetobacterium woodii*. Bacteria of the genus *Clostridium* are preferred, and *Clostridium autoethanogenum* is more preferred from the viewpoint of productivity of ethanol and long-term stability of culture.

In the present invention, the medium used for culturing the above microorganisms is not particularly limited as long as it has a composition suitable for the bacteria.

<Organic Substance and its Application>

Examples of organic substances produced by the method of the present invention include ethanol, 2,3-butanediol, acetic acid, lactic acid and isoprene. An organic substance including ethanol is preferred. The application of the organic substance produced is not particularly limited. The organic substance produced may be used as, for example, a raw material for plastics and resins, and can be used as various solvents, disinfectants or fuels. High concentration ethanol has an extremely wide range of applications, and can be used as, for example, a raw material for cosmetics, beverages, chemical substances and fuels (jet fuel), and an additive for foods other than fuel ethanol.

Next, the method for producing an organic substance in which the production apparatus of the present invention is involved will be described in detail.

II. Method for Production

<Raw Material Gas Production Step>

The raw material gas production step according to the present invention is a step of producing the raw material gas by gasification of the carbon source. For example, a fluidized bed furnace may be used as a gasifier, but the gasifier is not limited thereto. High heating rate in the hearth and excellent operationability are achieved when waste such as rubbish is partly burned. Gasification may be performed by heating (baking) waste in a low oxygen reducing condition at, for example, 450 to 600° C. and thermally decomposing it into gas (carbon monoxide, carbon dioxide, hydrogen, methane and the like) and char which contains a large amount of carbon. As described above, when gasification is performed in a fluidized bed furnace in an atmosphere at relatively low temperature and low oxygen, impurities in waste can be separated more hygienically and with lower oxidation degree than in the hearth, and thus metal in waste such as aluminum and iron can be selected and recovered without having been oxidized. Thus, utilizing such a process to achieve an efficient recycling of resources is another industrial advantage.

The temperature of the above gasification in the raw material gas production step in the present invention is usually 100° C. or more and 1500° C. or less, and preferably 200° C. or more and 1200° C. or less.

<Pretreatment Step>

The pretreatment step according to the present invention is a step of removing or reducing specific substances such as various pollutants, dust particles, impurities and compounds present in unfavorable amounts from the raw material gas, by passing the raw material gas through a certain scrubber and/or adsorption apparatus and the like before the synthesis gas feeding step.

In the present invention, it is particularly preferable that the pretreatment step includes a step of passing the raw material gas through a desulfurizer.

To perform the pretreatment step according to the present invention, the step may be configured using one or two or more devices of, for example, a scrubber (separator for water-soluble impurities) using water, an acidic solution or an alkaline solution, a gas chiller (water separator), a separator for fine particles (soot) such as a cyclone and a bag filter, a desulfurizer (separator for sulfide), a separator with a low temperature separation system (cryogenic system), a separator with a pressure swing adsorption system (PSA), a separator with a membrane separation system, a separator with a temperature swing adsorption system (TSA), a separator using activated carbon and a separator using a copper catalyst or a palladium catalyst.

The scrubber is used to remove pollutants and the like in gas. Any one of wet cleaning methods or dry cleaning methods may be used depending on the purpose. Of them, a wet cleaning method in which a particulate substance is brought into contact with a cleaning solution may be preferably used. An example thereof to be used is a cleaning method using what is called water curtain. In the case of using a wet cleaning method, the temperature of the solution is usually 40° C. or less, preferably 30° C. or less, more preferably 25° C. or less, and most preferably 15° C. or less.

An adsorption apparatus capable of adsorbing components other than carbon monoxide and hydrogen in the raw material gas may be used. Examples of units intended only for adsorption include a desulfurization layer and a deoxidization layer.

Of them, the desulfurization layer is not particularly limited as long as it can remove sulfur components. When sulfur components are not thoroughly removed from or reduced in the desulfurization layer and the amount of the sulfur components remains large, this may have a negative impact on an adsorption/desorption unit when there is such a unit at the subsequent stage.

Meanwhile, the deoxidization layer is not particularly limited as long as it can remove oxygen components. When oxygen components are not thoroughly removed or reduced in the deoxidization layer and the amount of the oxygen components remains large, anaerobic microorganisms used in the present invention may be killed.

Furthermore, an adsorption/desorption apparatus may be provided, and in such cases, any one of a PSA, a TSA and a PTSA may be preferably used. Any other units may be arbitrarily provided to further remove undesirable impurities.

Porous materials such as activated carbon, zeolite and molecular sieves and an aqueous solution such as an amine solution may be used as an adsorbing/desorbing material used in the adsorption/desorption apparatus. Of them, activated carbon or zeolite, which can adsorb aromatic compounds and sulfur compounds, is preferably used.

<Synthesis Gas Feeding Step>

The synthesis gas feeding step in the present invention is a step of feeding the above specific synthesis gas according to the present invention to a fermenter containing microorganisms, and is one of the very important steps in the method for production of the present invention.

The synthesis gas to be fed may contain components of the specific synthesis gas according to the present invention as described above. Such a synthesis gas may be prepared and fed to a fermenter. For example, as long as the condition of the component of the above synthesis gas is met, a gas obtained through the raw material gas production step and the subsequent pretreatment step may be directly used as synthesis gas. Alternatively, another certain gas may be added to the gas obtained through the raw material gas production step and the pretreatment step to use it as synthesis gas. At least one compound selected from the group consisting of a sulfur compound such as sulfur dioxide, a phosphorus compound and a nitrogen compound may be added as another certain gas to form synthesis gas.

<Fermentation Step>

The fermentation step according to the present invention is a step of microbial fermentation of synthesis gas in a fermenter. The fermenter contains the above microorganisms (species). Of them, some anaerobic microorganisms are known to produce an organic substance, which is a valuable such as ethanol, from substrate gas such as synthesis gas by their fermentation activity. These types of gas utilizing microorganisms are cultured in a liquid medium. It is preferable that the fermenter according to the present invention is a continuous fermentation apparatus. A microbial fermenter of any form may be usually used. Examples thereof include a stirring type, an airlift type, a bubble column type, a loop type, an open pond type and a photobioreactor type.

<Recovery Step>

The organic substance obtained by microbial fermentation in the fermentation step may be then subjected to a recovery step for the purpose of purification.

In the recovery step, treatment may be performed by, for example, a distiller, a treatment apparatus including a pervaporation membrane, a treatment apparatus including a zeolite dehydration membrane, a treatment apparatus for removing a low boiling point substance whose boiling point is lower than that of an organic substance, a treatment apparatus for removing a high boiling point substance whose boiling point is higher than that of an organic substance, and a treatment apparatus including an ion exchange membrane. For unit operation, heating distillation and membrane separation may be suitably used.

In the former heating distillation, a distiller may be used to recover the desired organic substance at high purity. The temperature in the distiller during distillation of an organic substance (particularly ethanol) is not particularly limited, but is preferably 100° C. or less, and more preferably about 70 to 95° C. Setting the temperature in the distiller at the above range ensures separation of the necessary organic substance from other components, i.e., distillation (recovery) of the organic substance.

The pressure in the distiller in distillation for an organic substance may be normal pressure, preferably less than atmospheric pressure, and more preferably about 60 to 95 kPa (gauge pressure). Setting the pressure in the distiller to the above range can improve the efficiency of separation of organic substances and thus can improve the yield of organic substances.

In the latter membrane separation, a known separation membrane may be suitably used. For example, a zeolite membrane may be preferably used.

In a preferred embodiment of the present invention, first a carbon source, waste, is gasified in the raw material gas production step, then a treatment with a scrubber, an adsorption treatment, a desulfurization treatment and a deoxidization treatment are performed in the pretreatment step, and a synthesis gas adjusted to meet the condition of the synthesis gas according to the present invention is fed to a fermenter in the synthesis gas feeding step, and then ethanol is produced by microbial fermentation (e.g., microbial fermentation using a *Clostridium* species) of the synthesis gas in the fermenter in the fermentation step.

EXAMPLES

The present invention will be described in more detail with reference to the following Examples, but the present invention is not limited to the following Examples.

<Method of Analysis>

The concentration of ethanol, which was obtained as an organic substance, was measured by liquid chromatography.

Reference Example 1

A continuous fermentation apparatus (fermenter) equipped with a main reactor, a synthesis gas feeding port, a medium feeding port and a discharge port was filled with an inoculum of *Clostridium autoethanogenum* (a microorganism) and a liquid medium for culturing the bacterium containing no sulfur compound (containing suitable amounts of a phosphorous compound, a nitrogen compound and various minerals and the like).

Next, gas composed of 40% of carbon monoxide, 5% of carbon dioxide, 45% of hydrogen and 10% of nitrogen, by volume (hereinafter referred to as reference gas), was prepared, and 50 ppm by volume of sulfur dioxide was added thereto to prepare a synthesis gas according to the present invention, and the synthesis gas was fed to the continuous fermentation apparatus together with the above liquid medium for culturing bacteria to continue culture (microbial fermentation).

Figure 4:
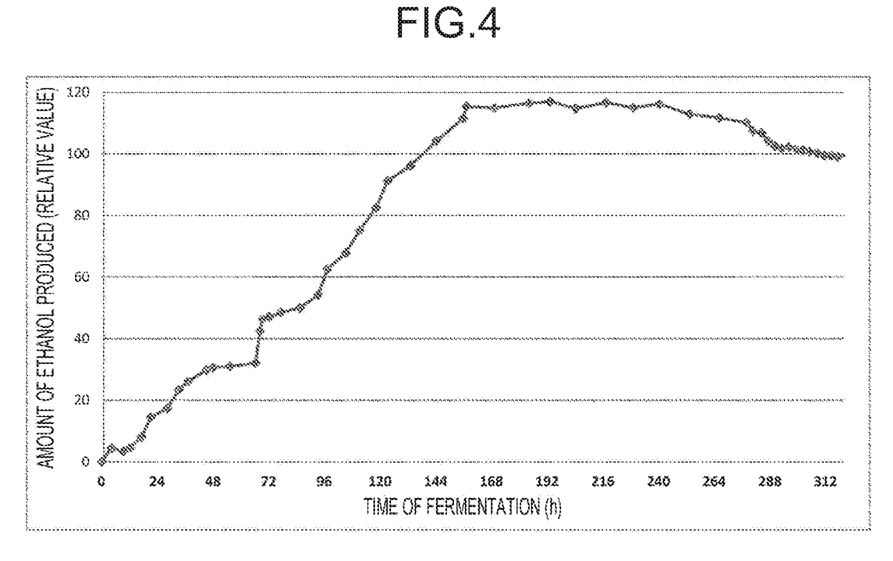
FIG. 4 is a view showing a change in the amount of ethanol produced relative to the time of fermentation in Reference Example 1.

The results are shown in FIG. 4. The amount of ethanol produced (vertical axis) in FIG. 4 is expressed as a relative value with the amount of ethanol produced 320 hours after the start of fermentation being 100.

As is clear from FIG. 4, the amount of ethanol produced continued to increase from the start of fermentation to the 157th hour (growth stage) and high productivity of ethanol was observed from the 157th hour to the 278th hour (initial high activity stage).

Then the amount of ethanol produced decreased, but was steady in the 278 to 320th hours again (stable stage).

This suggests that the bacteria can be cultured from inoculation to the production level in a stable manner even if the medium does not contain sulfur, which is an essential nutrient source.

This time only sulfur was fed as sulfur dioxide in the form of gas in the synthesis gas, but the same effect will probably be obtained even if a water-soluble phosphorus compound or nitrogen compound is fed in the same form of gas as the water-soluble sulfur dioxide.

Reference Example 2

Culture (microbial fermentation) was continued in the same manner as in Example 1 except for changing the synthesis gas fed to the continuous fermentation apparatus to a gas prepared by adding 1 ppm of sulfur dioxide and 1 ppm of xylene, by volume, to the above reference gas at the 320th hour from the start of fermentation. The results are shown in FIG. 5.

Figure 5:
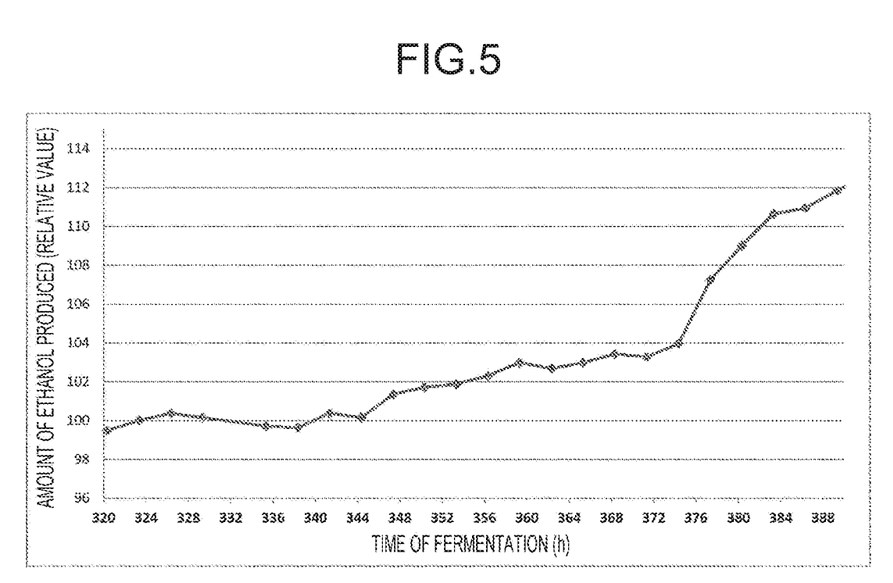
FIG. 5 is a view showing a change in the amount of ethanol produced relative to the time of fermentation in Reference Example 2.

As is clear from FIG. 5, the amount of ethanol produced at the 389th hour from the start of fermentation was 113, showing the effect of increasing the amount of ethanol produced of as high as 13% from that at the 320th hour.

This may be because a small amount of cytotoxic xylene in the synthesis gas put a moderate stress on cells, and thus improved the microbial activity in the fermenter.

Reference Comparative Example 1

Culture was performed in the same manner as in Example 1 except for changing the synthesis gas fed to the continuous fermentation apparatus to the above reference gas alone after 389 hours from the start of fermentation.

Figure 6:
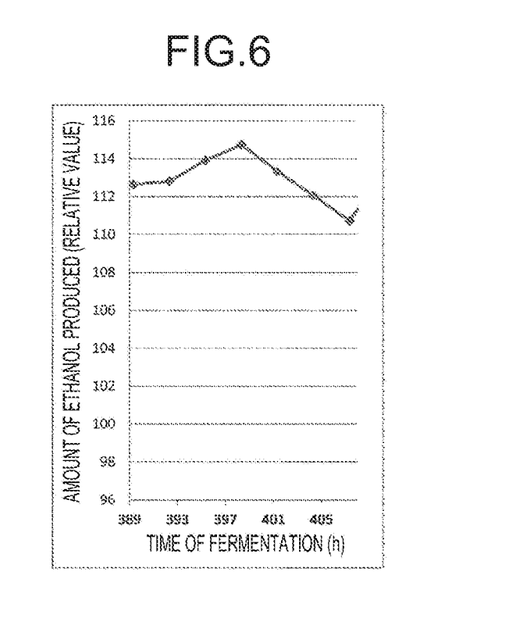
FIG. 6 is a view showing a change in the amount of ethanol produced relative to the time of fermentation in Reference Comparative Example 1.

The results are shown in FIG. 6.

As is clear from FIG. 6, the amount of ethanol produced suddenly decreased from 115 to 111 in only 9 hours from the 398th hour to the 407th hour.

This may be because the amount of nutrients in the fermenter, which are essential to microorganisms, became insufficient, beginning to induce a reduction of cell activity of microorganisms and cell death.

Reference Comparative Example 2

Culture (microbial fermentation) was performed in the same manner as in Example 1 except for changing the synthesis gas fed to the continuous fermentation apparatus to a gas prepared by adding 100 ppm of sulfur dioxide and 100 ppm of xylene, by volume, to the above reference gas at the 407th hour from the start of fermentation. The results are shown in FIG. 7.

Figure 7:
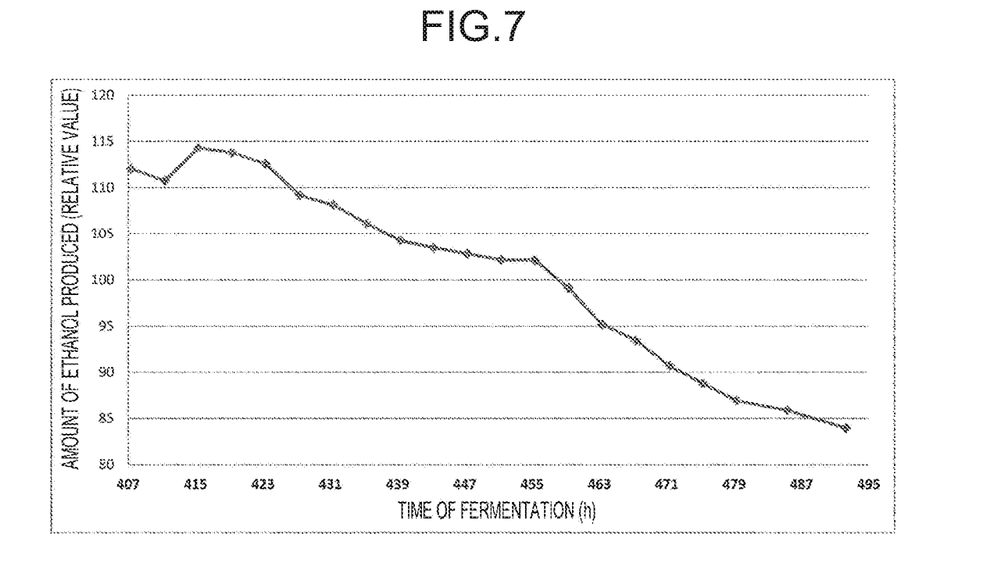
FIG. 7 is a view showing a change in the amount of ethanol produced relative to the time of fermentation in Reference Comparative Example 2.

As is clear from FIG. 7, although the amount of ethanol produced was temporarily steady at the 415th hour from the start of fermentation, thereafter the amount of ethanol produced suddenly decreased.

This may be because feeding of an excessive amount of sulfur dioxide increased acidity in the medium (culture solution) to cause cell death of microorganisms, and/or xylene caused cell death of microorganisms.

The method for producing an organic substance of the present invention has been described illustratively and non-limitedly with reference to preferred embodiments of the present invention above. Those skilled in the art should understand that modification and/or revision may be made without departing from the scope of the invention defined in the appended claims.

REFERENCE SIGNS LIST

1 Production apparatus
11 Raw material gas generating unit
12 Synthesis gas feeding unit
13 Fermenter
21 Gas circulating unit
22*a* First gas storage unit
22*b* Second gas storage unit
22*c* Third gas storage unit
23 Pressurizer

The invention claimed is:

1. An apparatus for producing an organic substance by microbial fermentation of a gas containing at least carbon monoxide and hydrogen, the apparatus comprising:
 a gas generating unit;
 a fermenter; and
 a gas circulating unit, wherein,
  the gas generating unit is coupled to an inlet of the gas circulating unit;
  the fermenter is coupled to an outlet of the gas circulating unit; and
  the gas circulating unit comprises:
   one or more upstream gas storage units, wherein the most upstream gas storage unit is coupled to the inlet of the gas circulating unit;
   one or more downstream gas storages units, wherein the most downstream gas storage unit is coupled to the outlet of the gas circulating unit; and
   a pressurizer coupled to the one or more upstream gas storage units and to the one or more downstream gas storage units.

2. The apparatus for producing an organic substance according to claim 1, wherein a capacity of at least one upstream gas storage unit is less than a capacity of at least one downstream gas storage unit.

3. The apparatus for producing an organic substance according to claim 1, wherein a capacity of a most upstream gas storage unit is half or less of a capacity of a most downstream gas storage unit.

4. The apparatus for producing an organic substance according to claim 1, wherein the apparatus comprises a carbon source coupled to the gas generating unit.

5. The apparatus for producing an organic substance according to claim 1, comprising a pretreatment unit, wherein the pretreatment unit is coupled to the gas generating unit and to the inlet of the gas circulating unit.

6. The apparatus for producing an organic substance according to claim 1, wherein the fermenter comprises a microorganism and a culture medium for the microorganism.

7. The apparatus for producing an organic substance according to claim 1, wherein the organic substance is ethanol.

8. The apparatus for producing an organic substance according to claim 4, wherein the carbon source comprises waste.

9. The apparatus for producing an organic substance according to claim 5, wherein, the pretreatment unit comprises a scrubber, an absorption apparatus, a separator, a desulfurizer, or a combination of any of the foregoing.

10. The apparatus for producing an organic substance according to claim 5, wherein, the pretreatment unit comprises a desulfurizer.

11. The apparatus for producing an organic substance according to claim 6 wherein, the microorganism comprises a *Clostridium* species.

12. The apparatus for producing an organic substance according to claim 6, wherein the culture medium does not comprise a sulfur compound.

13. The apparatus for producing an organic substance according to claim 1, comprising a synthesis gas feeding unit, wherein the synthesis gas feeding unit is coupled to the gas circulating unit outlet and to the fermenter.

14. The apparatus for producing an organic substance according to claim 1, wherein an outlet of a downstream gas storage unit is coupled to an inlet of an upstream gas storage unit.

15. The apparatus for producing an organic substance according to claim 1, wherein the gas circulating unit comprises:
- an upstream gas storage unit;
- a downstream gas storage unit;
- a pressurizer, wherein,
  - a pressurizer inlet is coupled to an outlet of the upstream gas storage unit; and
  - a pressurizer outlet is coupled to an inlet of the downstream gas storage unit; and
- wherein an outlet of the downstream gas storage unit is coupled to an inlet of the upstream gas storage unit.

16. The apparatus for producing an organic substance according to claim 1, wherein the gas circulating unit comprises:
- an upstream gas storage unit;
- a first downstream gas storage unit;
- a second upstream gas storage unit; and
- a pressurizer, wherein,
  - a pressurizer inlet is coupled to an outlet of the upstream gas storage unit;
  - a pressurizer outlet is coupled to an inlet of the downstream gas storage unit;
  - an outlet of the first downstream gas storage unit is coupled to an inlet of the second downstream gas storage unit;
  - a first outlet of the second downstream gas storage unit is coupled to the upstream gas storage unit; and
  - a second outlet of the second downstream gas storage unit is coupled to the synthesis gas feeding unit.

* * * * *